United States Patent [19]

Cavazza et al.

[11] Patent Number: 5,753,703
[45] Date of Patent: May 19, 1998

[54] PHARMACEUTICAL COMPOSITION COMPRISING L-CARNITINE OR AN ALKANOYL L-CARNITINE IN COMBINATION WITH A POLYUNSATURATED FATTY ACID OF THE OMEGA-3 SERIES FOR THE PREVENTION AND THE TREATMENT OF LIPID METABOLISM DISORDERS

[75] Inventors: Claudio Cavazza; Menotti Calvani, both of Rome, Italy

[73] Assignee: Sigma-Tau Industrie Farmaceutiche Riunite S.p.A., Rome, Italy

[21] Appl. No.: 755,310

[22] Filed: Nov. 22, 1996

[30] Foreign Application Priority Data

Dec. 21, 1995 [IT] Italy ................................ RM95A0835

[51] Int. Cl.$^6$ .................... A61K 31/205; A61K 31/20; A61K 31/22; A61K 31/195

[52] U.S. Cl. ..................... 514/556; 514/560; 514/551; 514/558; 514/561; 514/549

[58] Field of Search ........................ 514/556, 561, 514/549, 558, 560, 551

[56] References Cited

U.S. PATENT DOCUMENTS

| | | |
|---|---|---|
| 4,434,160 | 2/1984 | Jeretin et al. |
| 4,918,104 | 4/1990 | Weiss et al. |
| 5,013,443 | 5/1991 | Higashidate et al. |
| 5,412,113 | 5/1995 | Giannessi et al. |

*Primary Examiner*—William R.A. Jarvis
*Attorney, Agent, or Firm*—Oblon, Spivak, McClelland, Maier & Neustadt, P.C.

[57] ABSTRACT

A novel therapeutic use of L-carnitine or alkanoyl L-carnitine is disclosed in combination with a polyunsaturated fatty acid of the omega-3 series, for the prevention and the treatment of lipid metabolism disorders and cardiovascular disorders.

13 Claims, No Drawings

PHARMACEUTICAL COMPOSITION COMPRISING L-CARNITINE OR AN ALKANOYL L-CARNITINE IN COMBINATION WITH A POLYUNSATURATED FATTY ACID OF THE OMEGA-3 SERIES FOR THE PREVENTION AND THE TREATMENT OF LIPID METABOLISM DISORDERS

The present invention relates to a novel therapeutic use of L-carnitine, some alkanoyl L-carnitines and the pharmacologically acceptable salts thereof in combination with a polyunsaturated acid belonging to the omega-3 fatty acid series or ester thereof, particularly with eicosapentaenoic (EPA) or docosahexaenoic acid (DHA) or esters thereof or natural products or their extracts containing same, for the prevention and treatment of cardiovascular disorders, peripheral vascular diseases, diabetic peripheral neuropathy, shock, particularly anaphylactic and septic shock, and atherosclerotic, thromboembolic and tissutal disorders.

According to its broadest aspect, the invention relates to the coordinated use of L-carnitine or an alkanoyl L-carnitine or the pharmacologically acceptable salts thereof with a polyunsaturated acid belonging to the omega-3 fatty acid series or ester thereof, particularly EPA or DHA or esters thereof, or natural substances or their extracts containing same. By the "coordinated use" of the aforesaid compounds it is meant indifferently either the co-administration, i.e. the substantially concomitant supplementation of the aforesaid active ingredients, or the administration of a combination preparation containing a mixture of the aforesaid active ingredients, in addition to suitable excipients, if any.

The present invention also relates to orally, parenterally, rectally or transdermally administrable pharmaceutical compositions suitable for treating the aforesaid disorders which comprise, as active ingredients, L-carnitine or an alkanoyl L-carnitine or a pharmacologically acceptable salt thereof and a polyunsaturated acid belonging to the omega-3 fatty acid series or ester thereof, particularly with eicosapentaenoic (EPA) or docosahexaenoic acid or natural substances or extracts thereof containing same.

Since fish oil is particularly rich in EPA or DHA, it can be utilized as such in the compositions of the present invention.

The preferred EPA and DHA ester is the ethyl ester.

The compositions according to the invention may further comprise polyunsaturated acids contained in natural products such as propolis, behenic acid and seed corn oil.

In the compositions according to the invention the weight ratio between the polyunsaturated acid of the omega-3 fatty acid series or ester thereof, or natural products or extracts containing the same and L-carnitine or derivatives thereof, may range from 1:1 to 1:100.

The compositions according to the invention may further contain vitamins, mineral salts, antioxidizing agents and vegetal fibers. The compositions may take up a solid, semisolid, liquid, semiliquid, powder, granular or liposomic form, and occur as tablets, capsules, granulates, powders, vials for oral or parenteral administration.

The alkanoyl L-carnitines useful for the novel therapeutical use of the present invention are those wherein the alkanoyl group is a straight or branched group having from 2 to 8, preferably from 2 to 6 carbon atoms. Particularly preferred are acetyl, propionyl, butyryl, valeryl and isovaleryl L-carnitine.

Pharmaceutically acceptable salts of L-carnitine or alkanoyl L-carntine include, in addition to the inner salts, all the pharmaceutically acceptable salts which are prepared by the addition of an acid to L-carnitine or alkanoyl L-carnitine, respectively, and which do not give rise to undesirable toxic or collateral effects.

The formation of pharmaceutically acceptable acid addition salts is well known to the experts in pharmacy and pharmaceutical technology.

Non-limiting examples of suitable salts include the chloride, bromide, orotate, acid aspartate, acid citrate, acid phosphate, fumarate, acid fumarate, lactate, maleate, acid maleate, acid oxalate, acid sulphate, glucose phosphate, tartrate and acid tartrate salts.

For the sake of simplicity and clarity, hereinbelow reference will be made to L-carnitine only, it being understood, however, that whatever disclosed in connection with L-carnitine equally applies to the above-identified alkanoyl L-carnitines and pharmacologically acceptable salts thereof.

Previous therapeutical uses of L-carnitine are already known.

For istance L-carnitine has been used in the cardiovascular field in the treatment of acute and chronic myocardial ischaemia, angina pectoris, cardiac arrhythmias, insufficiency, and peripheral vascular diseases. In nephrology, L-carnitine has been administered to chronic uraemic patients who are subject to regular haemodialysis treatment with a view to counteracting muscular asthenia and the onset of muscular cramps.

Through fatty acid beta-oxydation L-carnitine is able to inhibit fat accumulation and provide for the energy cellular needs (Bremer Y., TIBS 2, 207, 1977) via modulation of extra- and intra-mitochondrial CoA.

The carnitines not only regulate bio-oxydation of the intramitochondrial fatty acids but also inhibit triglyceride formation (Bieber L. L. J. Biol. Chem. 254, 8163, 1979; Pande S. V., Proc. Nat. Acad. Sci. U.S.A. 72, 883, 1975).

Among the unsaturated fatty acids occuring in fish oil, eicosapentaenoic (EPA) and docosahexaenoic (DHA) acid were shown to be those mainly responsible for the therapeutic activity of fish oil.

Their efficacy was shown not only in preventing atherosclerosys (Kromhout e coll., N. Engl. J. Med., 312, 1205, 1985) but also arterial hypertension (Bonaa K. H., Bjerve K. S., Straume B., Gram I. T., Thelle D., N. Engl. J. Med., 322, 795, 1990), hypertriglyceridaemia (Miller Y. P., Heath I. D., Choraria S. K., Saymor R., Clin. Chim. Acta, 178, 251, 1988), thrombosis (Hansen Y. B., Olsen Y. O., Osternd B. Y., J. Intern. Med, 225, 133, 1989) renal diseases such as glomerulonephritis (Donadio Y. V., Bergstralh E., Spencer D., Holley K. E., N. Engl. J. Med., 18, 1194, 1994), psoriasis (Soiland E., Funk Y., Rayka G., Solvoll K., N. Engl. J. Med., 25, 1812, 1993), allergy (Lee T. H., Austen K. F., Am. Rev. Respir. Dis., 132, 1204, 1985), pulmonary emphysema (Shamar E., Folsour A. R., Melnick S., Higgins M. W., Szklo M., N. Engl. J. Med., 331, 228, 1994) and rheumatoid arthritis (Kremer Y. M., Yubiz W., Michael K. A, Ann. Int. Med., 106, 497, 1987).

It is well known that the incorporation of polyunsaturated fatty acids of the omega-3 series in cell membrane phospholipids such as those of platelets causes a reduction of the synthesis of thromboxane $A_2$ ($TXA_2$) aggregating factors, facilitating instead the synthesis of the biologically less active thromboxane $A_3$ ($TXA_3$).

At the same time, production of the more active prostacyclin $I_3$ is promoted, while the production of prostacyclin $I_2$ is reduced, thus further shifting the equilibrium of the reaction products in the antithrombotic and anti-atherosclerotic direction (M. Fischer, P. H. Levine, A. Leaf, Arch. Intern. Med., 149, 1726, 1989).

Leukotriene synthesis is also shifted in favour of the LTB$_5$ leukotrienes, which are far less active in the inflammation-promoting sense than the LTB$_4$ leukotrienes (T. H. Lee, Y. M. Mencia-Huerta, K. F. Austen, J. Biol. Chem., 259, 2383, 1984).

Important results for the purposes of more extensive knowledge of the effects of EPA and DHA are those demonstrating that their administration is capable of reducing the synthesis of interleukin-1 and of TNF (Tumour Necrosis Factor) whose role in the early stages of atherogenesis has been well documented (S. Endres, R. Ghabani, V. Kalley, C. A. Dinarello, N. Engl. J. Med., 320, 265, 1989), as well as being capable of promoting the formation of nitrous oxide by the endothelium, which may thus co-operate with the action of the other vascular vasodilator and antithrombogenic factors (Shinokawa et al., Circulation, 7, 898, 1987).

In addition, among the factors responsible for platelet aggregation and the consequent thrombotic reactions it should be recalled that an important role is also played by PAF (Platelet Activating Factor), the synthesis of which is also inhibited by the administration of polyunsaturated fatty acids (R. I. Sperling, Y. L. Relin, K. F. Austen, J. Immunol., 12, 4187, 1987).

It is known that to obtain the pharmacological and therapeutic effects described the daily administration of EPA and HDA needs to be both frequent and high-dose. This makes it difficult to achieve adequate patient compliance, also on account of the poor palatability of fish-oil derivatives.

There is, therefore, great interest in the possibility of enhancing the favourable therapeutic activities observed with EPA and DHA by reducing the doses needed and making their action more selective.

According to the invention described herein it has been found that the combination of L-carnitine or the alkanoyl L-carnitines or their previously mentioned salts with an acid of the omega-3 series and particularly with EPA and DHA, their esters, natural substances or their extracts containing them produces a surprising synergistic effect. Better therapeutic effects are thus achieved with a reduced use of the same active ingredients, with a consequent reduction in side effects, especially those related to the poor palatability of EPA and DHA. Patient compliance is also substantially enhanced.

In addition to these factors it should also be recalled that, by virtue of the well documented antilipoperoxidative activity of the carnitines, the presence of L-carnitine or its derivatives alongside polyunsaturated fatty acids of the omega-3 series may obviate one of the drawbacks stemming from the use of unsaturated fatty acids, namely their ability to undergo lipoperoxidation phenomena with the result that, in many formulations based on fatty acids of the omega-3 series, it has proved necessary to add antioxidising agents which may be either natural or artificial, but are devoid of positive pharmacological and metabolic interactions (O. Olivieri, M. Negri, P. Guerrini, R. Corrocher, Scand. J. Clin. Lab. Invest., 48, 659, 1988; S. Yla-Hertuala, Drugs of Today, 30, 507, 1994).

Reported here below are the toxicological results and the most significant pharmacological tests providing evidence of the unexpected synergistic action existing between the above-mentioned active ingredients according to the invention, which therefore lend themselves to various applications in the pharmaceutical or dietetic fields, or in the field of food supplements.

Toxicology

The toxicological tests have been conducted, combining L-carnitine and its derivatives with both fish-oil containing different concentrations of EPA and DHA and with the ethyl esters of EPA and DHA.

The different formulations were administered orally both to rats of the Wistar breed and to mice of the Swiss breed of both sexes. The LD$_{50}$ of the various combinations tested could not be established even after the administration of very high doses (10 to 100-fold greater than those administered in man), which is consistent with the well-known low toxicity of the components of the new composition.

The oral administration of 500 mg/kg of L-carnitine or its derivatives in combination with administration of 500 mg/kg or 1 g/kg of fish oil containing high percentages of EPA and DHA (18% and 12%, or 35% and 15%, respectively) failed, in fact, to produce any toxic effect or intolerance in the animals thus treated.

No evidence of toxic effects could be detected when combining L-carnitine or its derivatives with high doses of EPA and DHA ethyl esters (with a ratio between them of 75% to 15% per gram of polyunsaturated fatty acids).

Similar favourable results were achieved in the forms of chronic toxicity where no evidence of toxic intolerance reactions was found either in Wistar rats or in mice after chronic daily administration of 100 mg/kg of L-carnitine or its derivatives together with 500 mg/kg of fish oil with the highest concentrations of EPA and DHA for three consecutive months.

The various biological parameters observed relating to growth, survival or the blood-chemistry tests performed on the treated animals invariably proved comparable to those observed in control animals.

Pharmacological tests

Tests for protective activity against experimental atherosclerotic lesions

In these tests, experimental lesions were induced in Wistar rats according to a modified version of the method described by M. R. Malinow (Atherosclerosis 48, 105, 1983), which consists in the possibility of inducing atherosclerotic lesions by means of an atherogenic diet containing 24% casein, 10% cotton oil, 5% salt, 61% sugar, 2% cholesterol, and Vit D$_2$ 200 m STU/g diet.

This diet was administered for six weeks both to control rats and to rats treated with L-carnitine or acetyl L-carnitine or propionyl L-carnitine (100 mg/kg) or with fish oil (2 ml/kg of oil with percentages of EPA and DHA equal to 18 and 12%, respectively) or with EPA and DHA ethyl esters equal to 850 and 150 mg/kg, respectively.

In other groups of rats, in addition to the atherogenic diet, the treatment was given with L-carnitine or acetyl L-carnitine or propionyl L-carnitine or with fish oil or EPA and DHA ethyl esters or with these substances variously combined at the same doses as indicated above. At the end of the six-week treatment period all the animals, i.e. both controls and treated animals, were sacrificed. The atherogenic lesions induced were assessed using a morphometric method to measure the thickness of the abdominal aorta or the intensity of the staining induced by Sudan IV in the treated animals. Severity of lesions was scored using a scoring system from 1 to 5.

Only propionyl L-carnitine showed an assessable ability to reduce the intensity of the atherosclerotic damage induced, corresponding to a roughly 20% reduction, and a similar reduction was also found in the group of animals treated with fish oil or with EPA and DHA ethyl esters.

Very surprising, however, was the fact that no lesions were detectable in the group treated with propionyl L-carnitine and fish oil or its components (EPA and DHA ethyl esters). The inhibition of lesions observed in the other groups treated with fish oil plus acetyl L-carnitine or L-carnitine was greater than 50%, thus revealing a surprising degree of synergism between carnitines and polyunsaturated fatty acids of the omega-3 series.

Experimental hypertriglyceridaemia tests

A surprising synergistic effect between the carnitines, particularly propionyl L-carnitine, and omega-3 polyunsaturated fatty acids on experimental hypertriglyceridaemia was also detected.

These tests were performed in male Wistar rats with hypertriglyceridaemia experimentally induced by means of the oral administration of fructose according to the method described by L. A. Carlson (J. Atheroscler. Res., 8, 667, 1968—Atherosclerosis, 16, 349, 1972). In these tests, too, different groups of male Wistar rats were used and treated, over a 5-day period prior to the administration of 3 g of fructose, both with the various carnitines and with omega-3 polyunsaturated fatty acids or with combinations of these products at the same doses and according to the same procedures as in the tests performed to induce experimental atherosclerotic lesions.

Two hours after administration of fructose another dose of the products was administered both alone and in various combinations and five hours later the animals were sacrificed. The serum triglyceride test was performed according to the method described by R. K. Donabedian (Clin. Chem. 20, 632, 1974).

The results obtained in these tests also demonstrated a surprising degree of synergism between carnitines and omega-3 polyunsaturated oils.

Whereas, in fact, the effect on induced hypertriglyceridaemia is not significant either with the administration of carnitines or with that of polyunsaturated fatty acids, it becomes highly significant with combinations of the two groups of products. The inhibition achieved with L-carnitine plus fish oil is as much as 40%, whereas that with propionyl L-carnitine plus fish oil is greater than 60%.

Tests for protective activity in experimental thrombosis

In these tests, groups of Wistar rats were administered 300 mg/kg of L-carnitine orally or an equivalent dose of acetyl L-carnitine or propionyl L-carnitine every day for five consecutive days, while other groups of rats were treated orally for the same period of time with 2 ml/kg of fish oil (18% EPA and 12% DHA) or with 850 mg/kg and 150 mg/kg of EPA and DHA ethyl esters. In other groups of animals these various treatments were combined. After five days of treatment, in the various groups of animals thus treated as well as in the control group, experimental thrombosis was induced in the tail by injections of K-carrageenin (ET-1) according to the method described by A Bertelli (Drugs Exptl. Clin. Res., 19, 75, 1993). Both two and 24 hours after injection of the thrombogenic agents, significant degrees of protection were detectable in response to the carnitines (20%) and particularly propionyl L-carnitine (40%), while the protection afforded by both fish oil and the EPA and DHA ethyl esters was more limited.

A surprisingly high degree of protection was induced by the combination of L-carnitine and fish oil, which in some cases (propionyl L-carnitine plus fish oil) completely inhibited the onset of thrombosis, thus showing a powerful degree of synergism in blocking the action of the thromboembologenic factors and their related arterial necrotic phenomena.

Tests for release of cytoprotective and anti-inflammatory eicosanoids

The favourable changes in lipid metabolism induced both by carnitine and fish oil, as well as those relating to the formation and release of prostaglandin factors with an anti-inflammatory, cytoprotective and antithrombotic action, are also synergistically potentiated by the combined use of the various carnitines together with fish oil containing EPA and DHA.

This surprising degree of synergism has been demonstrated by oral administration of both L-carnitine and its derivatives and of fish oil or EPA and DHA esters (L-carnitine 300 mg/kg and/or fish oil 2 ml/kg or EPA and DHA ethyl esters 850 mg/kg and 150 mg/kg) to different groups of rats. At the end of the treatment period, peritoneal macrophages were isolated from all animals according to the method described by E. Schenkelaars (Int. J. Immunopharmacol., 8, 305, 1986) and then incubated with an ionophore (A-23187) stimulating the release of eicosanoids. After 30 minutes' incubation the cells were centrifuged and the eicosanoid content ($PGE_2$, $PGI_2$, $TXA_2$, $LTB_1$, $LTB_4$) of the supernatant was calculated by means of a radio-immunological method (F. J. Zijlska, J. E. Vincent, J. Chromatography, 311, 39, 1984) both in the rats treated with L-carnitine and in those treated with fish oil or EPA and DHA esters as well as in the groups treated with combinations of these products.

A reduction in aggregation-promoting, inflammatory eicosanoids was detected along with an increase in aggregation-inhibiting, anti-inflammatory eicosanoids. However, the formation of lipid products with a cytoprotective and anti-inflammatory anti-aggregant action ($PGE_2$, $PGI_2$) and the reduction of aggregation-promoting, inflammatory eicosanoids ($TXA_2$, $LTB_4$) proved surprisingly more marked in cells from the groups of animals treated with combinations of carnitines and fish oil, where the increase in production, particularly with the combinations containing propionyl L-carnitine, proved more than 100% greater than in control animals.

These results, therefore, also confirm that there is a surprising degree of synergism between carnitines and omega-3 polyunsaturated fatty acids in vivo in promoting the production of vascular protective and antithrombotic agents at the expense of inflammatory factors.

All the tests performed confirm a marked degree of synergism between carnitines and polyunsaturated fatty acids of the omega-3 series, and the results achieved are much more favourable than those obtainable when using the single components alone.

By way of examples, though the invention is in no sense limited to these, we give here below a number of possible formulations related to the invention described herein. For the purposes of brevity and simplicity, reference will be made only to L-carnitine, it being understood that the descriptions also apply to the above-mentioned alkanoyl L-carnitines and to the pharmacologically acceptable salts of both L-carnitine and the above-mentioned alkanoyl L-carnitines.

Examples of compositions

1. L-carnitine 250 mg, polyunsaturated fatty acids of fish 1 g (containing 350 mg of EPA and 150 mg of DHA), alpha-tocopherol acetate 1 mg.
2. L-carnitine 500 mg, polyunsaturated fatty acids of fish 1 g (containing 350 mg of EPA and 150 mg of DHA), alpha-tocopherol acetate 1 mg.
3. L-carnitine 250 mg, EPA ethyl ester 100 mg, DHA ethyl ester 150 mg, alpha-tocopherol acetate 1 mg.
4. L-carnitine 500 mg, EPA ethyl ester 100 mg, DHA ethyl ester 150 mg, alpha-tocopherol acetate 1 mg.
5. L-carnitine 250 mg, polyunsaturated fatty acids of fish 1 g (containing 350 mg of EPA and 250 mg of DHA), natural Vit. E. 1 mg, β-carotene 2 mg, selenium 0.05 mg, zinc 2.5 mg, magnesium 10 mg.
6. L-carnitine 250 mg, EPA ethyl ester 100 mg, DHA ethyl ester 150 mg, natural Vit. E. 1 mg, β-carotene 2 mg, selenium 0.05 mg, zinc 2.5 mg, magnesium 10 mg, cobalt 0.5 mg.
7. L-carnitine 500 mg, EPA ethyl ester 100 mg, DHA ethyl ester 150 mg, natural Vit. E. 1 mg, β-carotene 2 mg, selenium 0.05 mg, zinc 2.5 mg, manganese 1 mg, magnesium 10 mg, cobalt 0.5 mg.
8. L-carnitine 500 mg, EPA ethyl ester 100 mg, DHA ethyl ester 150 mg, natural Vit. E. 1 mg, β-carotene 2 mg, selenium 0.05 mg, zinc 2.5 mg, magnesium 10 mg, cobalt 0.5 mg.
9. L-carnitine 500 mg, polyunsaturated fatty acids of fish 1 g (containing 350 mg of EPA and 150 mg of DHA), corn oil 250 mg, lecithin of soya 250 mg, propolis 20 mg.

We claim:

1. An orally, parenterally, rectally or transdermally administrable pharmaceutical composition which comprises as active ingredients synergistic amounts of L-carnitine or an alkanoyl L-carnitine wherein the alkanoyl group, straight or branched, has 2–8 carbon atoms, or a pharmacologically acceptable salt thereof, and a polyunsaturated acid belonging to the omega-3 series or an ester thereof or natural products or extracts thereof containing same, and a pharmacologically acceptable excipient.

2. The composition of claim 1, wherein the alkanoyl L-carnitine is selected from acetyl, propionyl, butyryl, valeryl and isovaleryl L-carnitine.

3. The composition of claim 1 or 2 wherein the polyunsaturated acid belonging to the omega-3 series is eicosapentaenoic or docosahexaenoic acid or an ester thereof.

4. The composition of claim 3, wherein the ester of eicosapentaenoic or docosahexaenoic acid is the ethyl ester.

5. The composition of claim 1 wherein the natural product or extract thereof containing the polyunsaturated acid belonging to the omega-3 series is fish oil or an extract thereof.

6. The composition of claim 1 which further comprises one or more other polyunsaturated fatty acids contained in natural products.

7. The composition of claim 1 which further comprises one or more additives selected from the group consisting of vitamins, mineral salts, antioxidizing agents and vegetal fibers.

8. The composition of claim 1, in solid, semisolid, liquid, semiliquid, powder, granular or liposomic form, and occurring as tablets, capsules, granulates, powders and vials for the oral or parenteral administration.

9. A method for the treatment of cardiovascular, thromboaembolic, atherosclerotic disorders, peripheral vascular diseases, diabetic peripheral neuropathy or shock, comprising co-administering to a patient in need thereof an effective synergistic amount of both (1) L-carnitine or alkanoyl L-carnitine wherein the alkanoyl group, straight or branched, has 2–8 carbon atoms, or a pharmacologically acceptable salt thereof, and (2) an acid of the omega-3 series or an ester thereof or natural products or extract thereof containing same.

10. The composition of claim 1, wherein the alkanoyl group has 2–6 carbon atoms.

11. The composition of claim 6, wherein the polyunsaturated fatty acid is at least one of propolis, behenic acid and seed corn oil.

12. The method of claim 9, wherein the alkanoyl group has 2–6 carbon atoms.

13. The method of claim 9, wherein the shock is anaphylactic or septic shock.

* * * * *

(12) REEXAMINATION CERTIFICATE (4732nd)
United States Patent
Cavazza et al.

(10) Number: US 5,753,703 C1
(45) Certificate Issued: Feb. 11, 2003

(54) PHARMACEUTICAL COMPOSITION COMPRISING L-CARNITINE OR AN ALKANOYL L-CARNITINE IN COMBINATION WITH A POLYUNSATURATED FATTY ACID OF THE OMEGA-3 SERIES FOR THE PREVENTION AND THE TREATMENT OF LIPID METABOLISM DISORDERS

(75) Inventors: Claudio Cavazza, Rome (IT); Menotti Calvani, Rome (IT)

(73) Assignee: Sigma-Tau Healthscience S.p.A., Pomezia (IT)

Reexamination Request:
No. 90/006,085, Aug. 14, 2001

Reexamination Certificate for:
Patent No.: 5,753,703
Issued: May 19, 1998
Appl. No.: 08/755,310
Filed: Nov. 22, 1996

(30) Foreign Application Priority Data

Dec. 21, 1995 (IT) ........................................ RM95A0835

(51) Int. Cl.$^7$ .......................... A61K 31/20; A61K 31/22; A61K 31/195; A61K 31/205
(52) U.S. Cl. ........................ 514/556; 514/551; 514/556; 514/558; 514/560; 514/561
(58) Field of Search ................................ 514/549, 551, 514/556, 558, 560, 561

(56) References Cited

U.S. PATENT DOCUMENTS

| | | | |
|---|---|---|---|
| 4,526,902 A | 7/1985 | Rubin | 514/560 |
| 4,584,320 A | 4/1986 | Rubin | 514/560 |
| 5,231,085 A | 7/1993 | Alexander et al. | 514/44 |
| 5,631,288 A | 5/1997 | De Simone | 514/556 |

FOREIGN PATENT DOCUMENTS

| | | | |
|---|---|---|---|
| DE | 3721137 | 1/1989 | A61K/31/23 |
| DE | 3726299 | 2/1989 | A61K/31/23 |
| DE | 4012894 | 10/1991 | A61K/35/60 |
| EP | 232501 | 8/1987 | A61K/35/78 |
| EP | 627161 A1 | 12/1994 | A01N/1/02 |

OTHER PUBLICATIONS

*Biochemistry*, Voet and Voet (1990), pp. 658–659.

Definition of "Parenteral" from Webster's Third New International Dictionary (1993).

Definition of "Triglyceride" from Hawley's Condensed Chemical Dictionary, 13$^{th}$ Ed. (1997).

Definition of "Emulsion" from Hawley's Condensed Chemical Dictionary, 13$^{th}$ Ed. (1997).

"Fish Oil" entry in 1994 Biochemicals—Organic Compounds for Research and Diagnostic Reagents by Sigma Chemical Company.

*Fatty Acids and Their Derivatives*, A. W. Ralston (1948), p. 144.

Definition of "Fish Oil" from McGraw–Hill Dictionary of Scientific Technical Terms (5$^{th}$ Ed.) (1994).

*Primary Examiner*—Frederick Krass

(57) ABSTRACT

A novel therapeutic use of L-carnitine or alkanoyl L-carnitine is disclosed in combination with a polyunsaturated fatty acid of the omega-3 series, for the prevention and the treatment of lipid metabolism disorders and cardiovascular disorders.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 9 are determined to be patentable as amended.

Claims 2–8 and 10–13, dependent on an amended claim, are determined to be patentable.

1. An orally, parenterally, rectally or transdermally administrable pharmacetical composition which comprises as active ingredients synergistic amounts of [L-carnitine or] an alkanoyl L-carnitine wherein the alkanoyl group, straight or branched, has 2–8 carbon atoms, or a pharmacologically acceptable salt thereof, and a polyunsaturated acid belonging to the omega-3 series or an ester thereof or natural products or extracts thereof containing same, and a pharmacologically acceptable excipient.

9. A method for the treatment of cardiovascular, thromboaembolic, atherosclerotic disorders, peripheral vascular diseases, diabetic peripheral neuropathy or shock, comprising co-administering to a patient in need thereof an effective synergistic amount of both (1) [L-carnitine or] alkanoyl L-carnitine wherein the alkanoyl group, straight or branched, has 2–8 carbon atoms, or a pharmacologically acceptable salt thereof, and (2) an acid of the omega-3 series or an ester thereof or natural products or extract thereof containing same.

* * * * *